United States Patent [19]

Kaupmann et al.

[11] 4,009,184
[45] Feb. 22, 1977

[54] AMINO CARBONYL DERIVATIVES OF BENZOFURANS, PROCESSES FOR THEIR PRODUCTION, AND PHARMACEUTICAL COMPOSITIONS CONTAINING THE SAME 2-PHENYL-3-[3-DIALKYLAMINO-PROPANOYL]BENZOFURAN COMPOUNDS

[75] Inventors: Wilhelm Kaupmann, Hannover-Kirchrode; Klaus-Wolf von Eickstedt, Berlin; Salah-Eldin Rahman, Warnsdorf, all of Germany

[73] Assignee: Kali-Chemie Aktiengesellschaft, Hannover, Germany

[22] Filed: June 6, 1974

[21] Appl. No.: 477,091

[52] U.S. Cl. .................. 260/346.2 R; 260/268 BC; 260/293.58; 260/326.5 D; 260/247.7 T; 424/248.4; 424/250; 424/267; 424/274; 424/285
[51] Int. Cl.² .......................................... C07D 307/81
[58] Field of Search ............................ 260/346.2 R

[56] References Cited
UNITED STATES PATENTS 3,407,210  10/1968  Schoetensack et al. .... 260/346.2 R Primary Examiner—Henry R. Jiles
Assistant Examiner—Bernard Dentz
Attorney, Agent, or Firm—Michael J. Striker

[57] ABSTRACT

Compounds which are amino carbonyl derivatives of benzofurans which have the formula

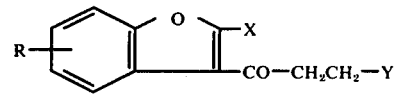

in which R is a hydrogen, halogen, or alkyl radical containing up to 4 carbon atoms, X is a phenyl, halophenyl, alkylphenyl, or alkoxyphenyl radical, the alkyl moieties of which contain up to 4 carbon atoms, and Y is a dialkylamino radical, the alkyl moieties of which contain up to 4 carbon atoms, or a pyrrolidino, piperidino, hexamethylenimino, morpholino, piperazino, 4-methylpiperazino, or 4-(2-hydroxyethyl)piperazino radical, and acid addition salts thereof, processes for their preparation, and pharmaceutical compositions containing these compounds.

10 Claims, No Drawings

AMINO CARBONYL DERIVATIVES OF BENZOFURANS, PROCESSES FOR THEIR PRODUCTION, AND PHARMACEUTICAL COMPOSITIONS CONTAINING THE SAME 2-PHENYL-3-[3-DIALKYLAMINOPROPANOYL]-BENZOFURAN COMPOUNDS

SUMMARY OF THE INVENTION

The present invention pertains to new and useful compounds which are amino carbonyl derivatives of benzofurans which have the following general formula

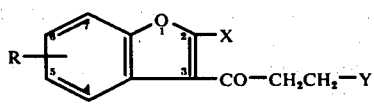

in which R is a hydrogen, halogen, or alkyl radical containing up to 4 carbon atoms, X is a phenyl, halophenyl, alkylphenyl, or alkoxyphenyl radical, the alkyl moieties of which contain up to 4 carbon atoms, and Y is a dialkylamino radical, the alkyl moieties of which contain up to 4 carbon atoms, or a pyrrolidine, piperidino, hexamethylenimino, morpholino, piperazino, 4-methyl-piperazino, or 4-(2-hydroxyethyl)piperazino radical, and their pharmaceutically acceptable salts with inorganic and organic acids.

The compounds of the present invention can be prepared by heating in a suitable solvent at an elevated temperature a mixture of a 2-phenyl-3-acetylbenzofuran having the following formula:

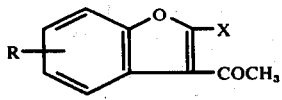

in which R and X each have the same significance as specified hereinbefore, formaldehyde, and a secondary amine of the group consisting of dialkylamines, the alkyl moieties of which contain up to 4 carbon atoms, or pyrrolidine, piperidine, hexamethylenimine having the formula

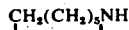

(which is also known as perhydroazepine) and 4-(2-hydroxyethyl)piperazine.

Suitable solvents include, for example, alkanols containing up to 5 carbon atoms, particularly ethanol and isopropanol. The secondary amines can suitably be added in the form of a salt, for example, as a hydrochloride. Other acids can also be added to the reaction mixture, for example, hydrogen chloride, which can be added in the form of a solution in the alkanol which is used as the solvent or in another alkanol.

The formaldehyde that is required in the reaction can be supplied in he form of a concentrated aqueous solution, or as paraformaldehyde, or as 1,3,5-trioxane.

The reaction itself is a typical Mannich reaction and the amino carbonyl derivatives of benzofurans that are thus produced can be accordingly referred to both as Mannich bases and Mannich ketones.

The amino moiety of the amino carbonyl derivatives of the benzofurans of the present invention can be exchanged for that of another secondary amine. Such an exchange or substitution reaction is appropriately carried out at a higher temperature and in a medium that is a solvent for the benzofuran, such as a lower alkanol, particularly ethanol or isopropanol. If the secondary amine is a liquid, it can itself serve as the medium for the reaction and, in order to obtain a good yield of the desired compound, the quantity of the secondary amine should be in excess of that stoichiometrically required for the desired exchange reaction.

The amino carbonyl derivatives of the benzofurans of the present invention can be purified by converting them into an acid addition salt and dissolving the acid addition salt in a suitable solvent, for example, a lower alkanol, and precipitating the compound in purer form therefrom by the addition of ethyl ether to the solution.

The acid addition salt can be converted to the free base by addition of an alkali to an aqueous solution of the acid addition salt and thereafter extracting the base that is thus precipitated from the aqueous solution by shaking the solution with ethyl ether. The ether extract is separated as a layer from the aqueous layer and the base dissolved therein is converted to the desired acid addition salt.

The 2-aryl-3-acetylbenzofurans that are required for the preparation of the compounds of the present invention are described for the most part in prior publications, although some are new compounds. A general method for the preparation of various 2-aryl-3-acetyl-benzofurans that was described by J.N. Chatterjea in the *Journal of Indian Chemical Society*, volume 34, pp. 347-356 (1957), consists in converting an arylbenzofuran with acetyl chloride in the presence of stannic tetrachloride. 2-Phenyl-3-acetylbenzofuran, 2-(p-tolyl)-3-acetylbenzofuran, and 2-(p-chlorophenyl)-3-acetylbenzofuran can be prepared in this manner. 2-Aryl-3-acetylbenzofurans can also be produced by the reaction of acetic anhydride on an acyl halide, particularly acetyl chloride, in a suitable solvent, such as ethyl acetate, in the presence of a catalytic amount of perchloric acid, with a 2-arylbenzofuran having the formula

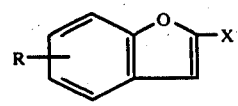

in which formula R and X each have the same significance as specified hereinbefore.

Acid addition salts of the amino carbonyl derivatives of benzofurans of the present invention may be prepared in conventional manner, for example, a solution of hydrogen chloride in ethanol or in another lower alkanol solvent may be added to a solution of the benzofuran derivative in ethyl ether. The hydrochloride is thus precipitated from the solution in the form of crystals. For the preparation of other similar nontoxic pharmaceutically acceptable acid salts, acetic acid, propionic acid, diethylacetic acid, malonic acid, succinic acid, fumaric acid, maleic acid, lactic acid, tartaric acid, malic acid, citric acid, sulfuric acid, hydrobromic acid, and orthophosphoric acid may be used.

DETAILED DESCRIPTION AND PREFERRED EMBODIMENTS OF THE INVENTION

The invention is further described in connection with the examples which follow, which however were selected solely for purposes of illustration and accordingly are to be understood not to be restrictive of the invention or its scope.

EXAMPLE 1

2-Phenyl-3-[3-(dimethylamino)propionyl]benzofuran.

To a solution of 20 grams of 2-phenyl-3acetylbenzofuran in 60 milliliters of isopropanol was added 3.6 grams of paraformaldehyde and 9.7 grams of dimethylamine hydrochloride and the mixture was heated under reflux for a period of 12 hours. The isopropanol was evaporated under vacuum from the resulting reaction mixture and the residue was taken up in a mixture of 100 milliliters of water and 20 milliliters of a 10% by weight aqueous hydrochloric acid solution. The resulting mixture was then shaken with ethyl ether to extract the undissolved portions therefrom and the aqueous layer was then separated from the ether layer. The resulting aqueous acid solution containing the hydrochloride was then made alkaline by addition thereto of a 5% aqueous solution of sodium hydroxide and the oily base which separated was extracted therefrom with ethyl ether and the ether extract was dried by the addition of anhydrous sodium sulfate thereto. To the resulting dried ether extract was added a solution of hydrogen chloride in ethanol in an amount in excess of that required stoichiometrically to form the hydrochloride of the desired compound that is named in the heading of this example. The hydrochloride separated from the resulting mixture in the form of crystals having a melting point of 148°-150°C. In this manner, 14.5 grams of the desired compound was obtained.

The hydrochloride that was thus recovered was further purified by dissolving it in ethanol and precipitating it from the resulting solution by the addition of 3 volumes of dry ethyl ether thereto, separating the precipitate by suction filtration.

The maleic acid addition salt of the compound was prepared by mixing together separate solutions in ethyl ether of equimolecular quantities of the benzofuran base compound and maleic acid. From this solution the maleic acid salt separated in the form of white crystals which, upon recrystallation from ethanol, had a melting point of 127°-128°C.

EXAMPLE 2

2-Phenyl-3-(3-piperidinopropionyl)benzofuran.

To a solution of 47.2 grams of 2-phenyl-3-acetylbenzofuran in 120 milliliters of isopropanol were added 6 grams of paraformaldehyde, 29.1 grams of piperidine hydrochloride and 6 milliliters of a saturated solution of hydrogen chloride in ethanol and the mixture was heated under reflux for a period of 10 hours. The solvent was evaporated from the resulting mixture under vacuum and the residue was triturated with ethyl ether. The portion of the residue that was insoluble in ether was separated from the ether extract and was dissolved in water. The aqueous solution was then made alkaline by addition thereto of a 5% aqueous solution of sodium hydroxide and the base that thus precipitated was extracted with ethyl ether and the extract was dried by addition of anhydrous sodium sulfate thereto. Upon addition to the ether extract of a solution of hydrogen chloride in ethanol, the hydrochloride of the compound named in the heading of this example precipitated, and it was separated by suction filtration and dried. it weighed 22.7 grams and, after recrystallization from ethanol, had a melting point of 173°-174°C.

EXAMPLE 3

2-Phenyl-3-(3-morpholinopropionyl)benzofuran.

A mixture of 23.6 grams of 2-phenyl-3- acetylbenzofuran, 70 milliliters of isopropanol, 4.2 grams of paraformaldehyde, and 17.3 grams of morpholine hydrochloride were heated under reflux at the boiling point for 12 hours, after which the solvent was evaporated therefrom under vacuum and the residue was triturated with dilute hydrochloric acid and the hydrochloride of the compound named in the heading of this example, which separated in the form of crystals therefrom, was separated from the mixture by suction filtration and dried. In this manner, 23.8 grams of the specified hydrochloride, which had a melting point of 177°-179°C, was obtained.

EXAMPLE 4

2-Phenyl-3-[3-(diethylamino)propionyl]benzofuran.

To a solution of 47.2 grams of 2-phenyl-3-acetyl benzofuran in 150 milliliters of isopropanol, were added 8.4 grams of paraformaldehyde, 30.8 grams of diethylamine hydrochloride and 3 milliliters of a saturated solution of hydrogen chloride in ethanol and the mixture was heated at its boiling point under reflux for 8 hours. The solvent was then evaporated from the mixture under vacuum and the residue was triturated with water and the insoluble portion thereof was extracted therefrom with ethyl ether. The aqueous solution was made alkaline by the addition of a 5% aqueous sodium hydroxide solution and the oily base which separated was extracted with ethyl ether. After drying the ether extract over anhydrous sodium sulfate a solution of hydrogen chloride in ethanol was added thereto and the crystalline hydrochloride of the compound named in the heading of this example precipitated. The crystals thus obtained were recrystallized in a mixture of ethanol and ethyl ether. In this manner, 34.2 grams of the recrystallized hydrochloride, which had a melting point of 113°-115°C, was obtained.

EXAMPLE 5

2-Phenyl-3-[3(N-methylpiperazino)propionyl]benzofuran.

To a solution of 23.6 grams of 2-phenyl-3-acetylbenzofuran in 100 milliliters of isopropanol were added 4.2 grams of paraformaldehyde and 19.1 grams of N-methylpiperazine dihydrochloride and the mixture was heated under gentle reflux for a period of 12 hours. The dihydrochloride of the compound named in the heading of this example precipitated from the reaction mixture and was separated therefrom by suction filtration, washed with a small quantity of ethanol, and recrystallized from ethanol. The dihydrochloride had a melting point of 174°-177°C and 22.8 grams thereof was thus obtained.

EXAMPLE 6

2-Phenyl-3-(3-pyrrolidinopropionyl)benzofuran.

To a solution of 23.6 grams of 2-phenyl-3-acetylbenzofuran in 70 milliliters of isopropanol was added 4.2 grams of paraformaldehyde, 10 grams of pyrrolidine and 30 milliliters of a saturated solution of hydrogen chloride in ethanol and the mixture was heated under reflux at its boiling point for 10 hours.

The solvent was thereafter evaporated under vacuum from the mixture and the residue was triturated with water and the portion of the residue that was not dissolved in the water was separated by extraction of the suspension with ethyl ether. The aqueous solution was then made alkaline by the addition of a 5% aqueous sodium hydroxide solution thereto and the oily base that precipitated was extracted by shaking the mixture with ethyl ether. The ethyl ether layer was then separated from the aqueous layer, washed with several portions of water, and dried over anhydrous sodium sulfate. A solution of hydrogen chloride in ethanol was then added to the dried ether extract and the crystals of the hydrochloride of the compound named in the heading of this example that precipitated were separated by suction filtration and recrystallized from a mixture of methanol and ethyl ether. In this manner, 14.4 grams of the hydrochloride, which had a melting point of 138°-140°C, was obtained.

EXAMPLE 7

2-Phenyl-3-[3-(hexamethylenimino)propionyl]benzofuran.

A mixture of 11.8 grams of 2-phenyl-3-acetylbenzofuran, 30 milliliters of isopropanol, 2.1 grams of paraformaldehyde and 9.5 grams of hexamethylenimine hydrochloride was heated under reflux for a period of 6 hours. The solvent was then evaporated from the reaction mixture under vacuum and the residue was triturated with water. Thereafter a mixture of equal volumes of benzene and ethyl acetate was added to the aqueous suspension and the mixture was heated to a temperature of 50° C. The aqueous phase was then separated from the resulting mixture and was made alkaline by the addition thereto of a 5% aqueous solution of sodium hydroxide, whereupon an oily base separated. Benzene was added to the resulting suspension and shaken therewith to dissolve an thereby extract the oily base. Benzene was then evaporated from the extract and a solution of hydrogen chloride dissolved in ethanol was then added to the residue to convert it to the hydrochloride. The resulting hydrochloride of the compound named in the heading of this example, after recrystallization from ethanol, weighed 6.4 grams and melted with decomposition at a temperature of 144° C.

EXAMPLE 8

2-Phenyl-3-3- 3-[N-(2-hydroxyethyl)piperazino]pripionyl benzofuran.

A solution of 26.4 grams of 2-phenyl-3[3-(dimethylamino) propionyl]benzofuran hydrochloride, whose preparation was described in Example 1, and 26 grams of N-(2-hydroxyethyl)piperazine in 80 milliliters of isopropanol was heated under reflux for a period of 5 hours while the solution was maintained under a blanket of nitrogen. The solvent was evaporated from the resulting reaction mixture under vacuum and the residue was triturated with a 5% aqueous solution of sodium hydroxide and the resulting mixture was extracted with ethyl acetate. The ethyl acetate extract was then separated from the aqueous solution and washed with several portions of water and dried over anhydrous sodium sulfate. The dried extract was evaporated under vacuum to expel the ethyl acetate and a solution of hydrogen chloride in ethanol was then added to the residue to convert it to the dihydrochloride of the compound named in the heading of this example. The resulting dihydrochloride, after recrystallization from methanol, had a melting point of 181°-183° C and weighted 21.2 grams.

EXAMPLE 9

2-Phenyl-3-[3-(dimethylamino)propionyl]-5-methylbenzofuran.

A mixture of 62.4 grams of 2-phenyl-5-methylbenzofuran, 300 milliliters of ethyl acetate, 57 milliliters of acetic anhydride, and 3 milliliters of 70% perchloric acid was allowed to stand for 2 days at room temperature during which period 2-phenyl-3-acetyl-5-methylbenzofuran precipitated therefrom. The precipitate was then separated from the mixture by suction filtration. The filtrate was washed with several portions of water and the ethyl acetate was evaporated therefrom and the residue thus obtained was combined with the original precipitate and distilled therefrom at an absolute pressure of 1 torr, its boiling point at this pressure being 160°-163° C. The distilled product was recrystallized from ethanol to yield 42.8 grams of crystals having a melting point of 118.5°-120.5° C.

A suspension in 60 milliliters of isopropanol of 21.3 grams of the 2-phenyl-3-acetyl-5-methylbenzofuran that was thus prepared, 3.9 grams of paraformaldehyde, 10.4 grams of dimethylamine hydrochloride, and 8 milliliters of a saturated solution of hydrogen chloride in ethanol was heated under reflux for a period of 8 hours, after which the solvent was evaporated therefrom under vacuum and the remaining residue was treated with 20 milliliters of a 10% aqueous hydrochloric acid solution. The undissolved portion was extracted from the solution in which it was suspended with ethyl ether and the aqueous phase was then separated and made alkaline by the addition thereto of a 5% aqueous solution of sodium hydroxide. The oily base that precipitated was then extracted with ethyl ether, washed with water and dried over anhydrous sodium sulfate. A solution of hydrogen chloride in ethanol was then added to the dried ether extract and the precipitate consisting of the hydrochloride of the compound named in the heading of this example was separated therefrom by suction filtration. The precipitate, after recrystallization from a mixture of ethyl ether and ethanol, had a melting point of 148°-149° C and weighed 22.5 grams.

EXAMPLE 10

2-Phenyl-3-[3-(hexamethylenimino)propionyl]-5-methylbenzofuran.

A mixture of 21.3 grams of 2-phenyl-3-acetyl-5-methylbenzofuran, 3.9 grams of paraformaldehyde, 17.4 grams of hexamethylenimine hydrochloride, 80 milliliters of isopropanol and 8 milliliters of a saturated solution of hydrogen chloride in ethanol was heated under reflux for a period of 8 hours, after which the solvent was evaporated therefrom under vacuum. The residue consisted of a crystalline mass of the hydrochloride of the compound named in the heading of this example. The crystalline mass was triturated with a small quantity of water and then dried on a suction filter. The dried crystals were redissolved in ethanol and precipitated by addition of ethyl ether to the solution in ethanol. In this manner, 22.1 grams of the hydrochloride, having a melting point of 143.5°–145.5° C, was obtained.

EXAMPLE 11

2-Phenyl-3-[3-(dimethylamino)propionyl]-7-methylbenzofuran.

To a solution of 100 grams of 2-phenyl-7-methylbenzofuran in 480 of ethyl acetate was added 91 milliliters of acetic anhydride and 5 milliliters of 70% perchloric acid and the mixture was allowed to stand for 17 hours at room temperature. Thereafter the mixture was washed with several portions of water and dried over anhydrous sodium sulfate, after which the ethyl acetate was evaporated therefrom under vacuum and the remaining 2-phenyl-3-acetyl-7-methylbenzofuran was distilled under an absolute pressure of 0.5 torr. The boiling point of the compound at that pressure was 170°–180° C and, after recrystallization from methanol, 75.6 grams of crystals thereof having a melting point of 84°–85.5° C, were obtained.

To a suspension of 10 grams of the 2-phenyl-3-acetyl-7-methylbenzofuran that was thus prepared in 40 milliliters of isopropanol was added 1.7 grams of paraformaldehyde, 4.6 grams of dimethylamine hyrochloride, and 4 milliliters of a saturated solution of hydrogen chloride in ethanol, and the mixture was heated at its boiling point for a period of 10 hours. The solvent was then evaporated from the mixture under vacuum and the residue was taken up in water, and the insoluble portions of the residue were extracted from the resulting solution with ethyl ether. The aqueous solution was then made alkaline by the addition thereto of a 5% aqueous solution of sodium hydroxide and the precipitated base was extracted therefrom by the addition of ethyl ether thereto. The ethyl ether extract was separated and dried over anhydrous sodium sulfate. A solution of hydrogen chloride in ethanol was then added to the dried ether extract, whereupon crystals of the hydrochloride of the compound named in the heading of this example precipitated therefrom. The crystals were separated by suction filtration and recrystallized from a mixture of ethanol and ethyl ether. In this manner, 13.2 grams of crystals of the hydrochloride, having a melting point of 145°–146.5° C, was obtained.

EXAMPLE 12

2-(p-Tolyl)-3-[3-(dimethylamino)propionyl]benzofuran.

To a solution of 20 grams of 2-(p-tolyl)-3-acetylbenzofuran in 80 milliliters of isopropanol was added 3.4 grams of paraformaldehyde, 9.1 grams of dimethylamine hydrochloride, and 8 milliliters of a saturated solution of hydrogen chloride in ethanol, and the mixture was heated under gentle reflux for a period of 8 hours. The solvent was evaporated under vacuum and the residue was taken up in water and ethyl ether was then added thereto to dissolve and extract the water-insoluble solids from the solution. The ether extract was then separated from the aqueous layer and the aqueous layer was made alkaline by the addition thereto of a 5% aqueous solution of sodium hydroxide. The precipitated oily base was then extracted with ethyl ether from the aqueous solution, washed with several portions of water, and dried over anhydrous sodium sulfate. A solution of hydrogen chloride in ethanol was then added to the dried ether extract and the crystals of the hydrochloride of the compound named in the heading of this example which were thus precipitated were separated by suction filtration and recrystallized by dissolving them in ethanol and precipitating them by the addition of ethyl ether to the ethanol solution. In this manner, 9.1 grams of the hydrochloride, which had a melting point of 136°–138° C, was obtained.

EXAMPLE 13

2-(p-Chlorophenyl)-3-[3-dimethylamino)-propionyl]-benzofuran.

A mixture of 23.8 grams of 2-(p-chlorophenyl)-3-acetylbenzofuran, 65 milliliters of isopropanol, 3.7 grams of paraformaldehyde, and 10.0 grams of dimethylamine hydrochloride was heated under reflux for a period of 24 hours. After cooling, the crystals which precipitated from the solution were separated by suction filtration and dissolved in methanol. The methanol solution was filtered to separate the insoluble solids therefrom and ethyl ether was then added thereto to precipitate crystals of the hydrochloride of the compound named in the heading of this example. The precipitated crystals were then separated by suction filtration and dried. In this manner, 15.0 grams of crystals of the hydrochloride, having a melting point of 161°–163° C, was obtained.

EXAMPLE 14

2-Phenyl-3-[3-(dimethylamino)propionyl]-7-chlorobenzofuran.

To a solution of 34.6 grams of 2-phenyl-7-chlorobenzofuran in 145 milliliters of ethyl acetate, were added 27 milliliters of acetic anhydride, and 1.5 milliliters of 70% perchloric acid, and the mixture was allowed to stand for 3 days at room temperature. The mixture was then washed with several portions of water and dried over anhydrous sodium sulfate and the ethyl acetate was evaporated therefrom and the residue was then distilled at an absolute pressure of 0.3 torr, boiling within the range between 170° and 180° C at that pressure. After cooling, the distillate consisting of 2-phenyl-3-acetyl-7-chlorobenzofuran was recrystallized from ethanol. There was thus obtained 27.0 grams of crystals having a melting point of 109°–110° C.

To a suspension of 23 grams of the 2-phenyl-3-acetyl-7-chlorobenzofuran that was thus produced in 60 milliliters of isopropanol were added 3.9 grams of paraformaldehyde, 10.4 grams of dimethylamine hydrochloride, and 8 milliliters of a saturated solution of hydrogen chloride in ethanol and the mixture was heated under reflux for a period of 8 hours. The solvent was then evaporated under vacuum and the residue was taken up in water and the remaining water-insoluble material was extracted from the resulting solution with ethyl ether. A 5% aqueous solution of sodium hydroxide was then added to the aqueous solution until it was alkaline and the oily base had precipitated. Ethyl ether was then added to the aqueous solution to extract the oily base and the aqueous phase was separated therefrom. The ether extract was then dried over anhydrous sodium sulfate and a solution of hydrogen chloride in ethanol was then added thereto, producing a precipitate of the hydrochloride of the compound named in the heading of this example. The hydrochloride was then separated by suction filtration and recrystallized from ethanol, yielding 21.7 grams of crystals having a melting point of 163°–164° C.

EXAMPLE 15

2-Phenyl-3-(3-piperidinopropionyl)-7-chlorobenzofuran.

To 100 milliliters of isopropanol containing 36.4 grams of 2-phenyl-3-[3-(dimethylamino)pripionyl]-7-clorobenzofuran hydrochloride was added 25 milliliters of piperidine. The mixture was heated under reflux for a period of 4 hours while it was maintained under a blanket of nitrogen. The isopropanol was evaporated under vacuum and the residue was stirred together with 250 milliliters of a 10% aqueous solution of sodium hydroxide. From the resulting solution the precipitated oily base was extracted with ethyl ether and the ether extract was washed twice with portions of water, dried over anhydrous sodium sulfate, and the ether was evaporated therefrom. The residue consisting of the oily base was then dissolved in dry ethyl ether and a solution of hydrogen chloride in ethanol was added thereto, producing a precipitation of the hydrochloride of the compound named in the heading of this example, which was separated by suction filtration and recrystallized from ethanol. The crystals of the hydrochloride thus obtained had a melting point of 170°–172° C and a total weight of 12.0 grams.

EXAMPLE 16

2-(p-Methoxyphenyl)-3[3-(dimethylamino)-propionyl]benzofuran

To a solution of 60 grams of 2-(p-methoxyphenyl)-benzofuran in 500 milliliters of ethyl acetate were added 60 milliliters of acetic anhydride and 3.3 milliliters of 70% perchloric acid and the mixture was allowed to stand for 3 days at room temperature, during which period crystals of 2-(p-methoxyphenyl)-3-acetylbenzofuran formed therein. The crystals were separated by suction filtration, washed with water and, after drying, were recrystallized from methanol. There was thus obtained 17.3 grams of crystals having a melting point of 76°–77° C.

To a solution of 9.3 grams of the 2-(p-methoxyphenyl)-3-acetylbenzofuran that was thus produced in 30 milliliters of isopropanol were added 1.4 grams of paraformaldehyde and 4.1 grams of dimethylamine hydrochloride and the mixture was heated under reflux for a period of 12 hours. The solvent was then evaporated under vacuum and the residue was taken up in a 5% aqueous solution of hydrochloric acid. The acid solution was then extracted with benzene and the aqueous solution that had thus been freed of benzene-soluble substances was then made alkaline by the addition thereto of a 5% aqueous solution of sodium hydroxide, thereby precipitating the oily base. The solution containing the precipitated oily base was then extracted with ethyl ether, the ether extract was dried over anhydrous sodium sulfate, and a solution of hydrogen chloride in ethanol was added thereto, thereby precipitating the hydrochloride of the compound named in the heading of this example, which was separated by suction filtration. After recrystallization from ethanol, 6.5 grams of crystals of the hydrochloride, which had a melting point of 161°–162.5° C, was thus obtained.

EXAMPLE 17

2-Phenyl-3-[3-dimethylamino propionyl]-5-chlorobenzofuran.

To a solution of 76.2 grams of 2 phenyl-5-chlorobenzofuran in 330 milliliters of ethyl acetate were added 62.5 milliliters of acetic anhydride, and 3.3 milliliters of 70% perchloric acid and the mixture was heated under reflux for 7 hours. The mixture was then shaken and extracted several times with fresh volumes of water and then dried over anhydrous sodium sulfate. The solvent was then evaporated from the resulting dried solution and the residue was vacuum distilled at an absolute pressure of 0.3 torr, the fraction within the range between 182° and 195° C at this pressure being collected. The distillate, consisting of a yellow oil, crystallized when triturated with petroleum naphtha. After recrystallization from petroleum ether, 63.7 grams of crystals, which had a melting point of 71°–73° C, was obtained.

To a solution of 13.5 grams of the 2-phenyl-3-acetyl-5-chlorobenzofuran that was thus prepared in 35 milliliters of isopropanol were added 2.1 grams of paraformaldehyde and 5.7 grams of dimethylamine hydrochloride and the mixture was heated for 16 hours under reflux. The solvent was then evaporated therefrom under vacuum and the residue was taken up in a 5% aqueous solution of hydrochloric acid. The substances that remained undissolved in the hydrochloric acid were extracted therefrom with ethyl ether. The aqueous solution was then made alkaline by the addition of a 5% aqueous solution of sodium hydroxide, whereupon the oily base separated. The solution containing the oily base was then shaken with ethyl ether and the ethyl ether extract was separated therefrom, dried over anhydrous sodium sulfate, and a solution of hydrogen chloride in ethanol was added thereto, whereupon crystals of the hydrochloride of the compound named in the heading of this example separated. After recrystallization from ethanol, 8.1 grams of crystals, which had a melting point of 153°–155° C, was obtained.

UTILITY OF THE COMPOUNDS OF THE PRESENT INVENTION

In animal experiments the compounds of the present invention proved to have characteristics that are typical of clinically useful antidepressants 2-Phenyl-3-[3-(dimethylamino)propionyl]benzofuran hydrochloride which was disclosed in Example 1 hereinbefore was subjected to extensive testing in this respect.

In mice, 2-phenyl-3-[3-(dimethylamino)propionyl]-benzofuran was observed to inhibit the action of reserpine. Peroral administration of the compound in doses equivalent to 35 milligrams per kilogram of body weight produced a 50% inhibition of reserpine induced ptosis.

The inhibition of catalepsy produced by reserpine was further tested in mice. Mice were injected intraperitoneally with a dose of reserpine equivalent to 4.64 milligrams per kilogram. After 60 minutes the mice were placed upon a climbing bar and after 30 seconds the extent of catalepsy was observed and the test compound was administered perorally to the animal. It was found that in this test a dose of 100 milligrams of the compound per kilogram of body weight produced a 50% inhibition of the catalepsy produced by reserpine within a period of 240 minutes.

In the same manner, animal tests were performed on mice to determine the effectiveness of the compound in inhibiting catalepsy produced by tetrabenazine (2-oxo-3-isobutyl-9,10-dimethoxy-1,2,3,4,6,7-hexahydro-11bH-benzo[a]quinolizine). All animals were injected intraperitoneally with a dose of 68.1 milligrams of tetrabenazine per kilogram of body weight. The tetrabenazine was administered in the form of a suspension containing 1% by weight of tragacanth.

After 60 minutes the animals were placed upon a climbing bar and after 30 seconds the extent of catalepsy was observed and the test compound was administered perorally to the animal. It was found that in this test a dose of 100 milligrams of the compound per kilogram of body weight produced a 45% inhibition of the catalepsy produced by tetrabenazine within a period of 240 minutes.

In the amphetamine-group toxicity test, it was found that 300 milligrams of the compound per kilogram of body weight administered perorally increased the $LD_{16}$ of amphetamine sulfate to $LD_{50}$.

The compound produced an increase of "gnawing rate" (Zwangsnagen) in mice induced by a dose of apomorphine.

The prolonging of sodium hexobarbital induced sleeping time by the compound in mice was tested at dosages ranging from 21.5 to 100 milligrams per kilogram of body weight which were administered perorally. In these tests, a dose equivalent to 64 milligrams of sodium hexobarbital per kilogram of body weight of the mouse was injected intravenously into the mouse 30 minutes after the compound had been administered perorally. The duration of sleeping time is then observed. It was found that, when a dosage of 46.4 milligrams per kilogram of body weight of the compound was administered perorally, the duration of sleeping time was twice that produced when only sodium hexobarbital was administered to the mouse.

A test based on the amount of degradation of kynurenine (3-anthraniloylalanine) in the liver of rats was used to determine whether th compound when administered perorally to rats inhibited the monoaminooxidase system. In dosage ranges between 2.15 and 316 milligrams per kilogram of body weight in in vito tests no differences in the rate of oxidative deamination of kynurenine was observable between the control and the test animals. The compound does not inhibit the monoaminooxidase system.

In tests of acute toxicity performed in accordance with the method described by J. T. Litchfield and F. Wilcoxon in Journal of Pharmacology and Experimental Therapeutics, volume 96, page 99 (1949), the lethal dose ($LD_{50}$) of 2-phenyl-3-[3-(dimethylamino)propionyl]benzofuran hydrochloride in mice was found to be 1230 milligrams per kilogram of body weight when administered perorally, and 137 milligrams per kilogram when administered intraperitoneally.

In the treatment of depression in humans, preparations are administered which besides stimulating the central nervous system also have a sedative effect. The compounds of the present invention provide both these therapeutic effects. What is particularly notable about the compounds of the present invention is their very low toxicity, as a consequence of which a broad therapeutic range can be expected.

In a clinical investigation of patients with predominantly endogenous depression, 2-phenyl-3-[3-(dimethylamino)pripionyl]benzofuran hydrochloride had a distinct action against agitation combined with feelings of guilt. Its effectiveness can be subdivided as follows:

[1] strong suppression of excitability parallel to normalization of initiative

[2] mild sedation

[3] significant brightening of mood

No serious side effects of the compound were observed.

The compounds can be used with the usual pharmaceutically acceptable diluents or carrier materials such as cellulose, starch, polyethylene glycol, magnesium stearate or talcum. Water-soluble compounds can also be administered as aqueous solutions. If the compounds are water insoluble they may be administered in the form of suspension for instance in 1% methyl cellulose (tylose) solution. They can be administered per os or parenterally to human patients.

In the treatment of human patients dosages ranging between 25 and 100 milligrams of the compound when administered perorally three times daily normally effective.

Tablets are prepared according to the following procedure:

| Base material | per charge |
|---|---|
| KF 407-Active component | 100,0 g |
| Colloidal Silicondioxide 200 | 4,0 g |
| Microcristalline Cellulose PH 101 | 200,0 g |
| Formaldehyde-Casein | 20,0 g |
| Magnesiumstearate | 4,0 g |
| Lactose | 50,0 g |
| Polyethylenglycol 4000 | 12,0 g |
| Talc | 10,0 g |
| | 400,0 g |

Without further analysis, the foregoing will so fully reveal the gist of the present invention that others can, by applying current knowledge, readily adapt it for various applications without omitting features that, from the standpoint of prior art, fairly constitute esential characteristics of the generic or specific aspects of this invention.

What is claimed as new and desired to be protected by Letters Patent is set forth in the appended claims:

1. An amino carbonyl benzofuran of the group consisting of compounds having the formula

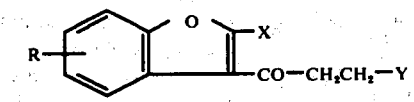

in which R is hydrogen, halogen, or alkyl containing up to 4 carbon atoms, X is phenyl, halophenyl, alkylphenyl, or alkoxyphenyl, the alkyl moieties of which contain up to 4 carbon atoms, and Y is a dialkylamino radical, the alkyl moieties of which contain up to 4 carbon atoms, and pharmaceutically acceptable acid addition salts thereof.

2. A compound as defined in claim 1 which is 2-phenyl-3-[3-(dimethylamino)propionyl]benzofuran.

3. A compound as defined in claim 1 which is 2-phenyl-3-[3-(diethylamino)propionyl]benzofuran.

4. A compound as defined in claim 1 which is 2-phenyl-3-[3-(dimethylamino)propionyl]-5-methylbenzofuran.

5. A compound as defined in claim 1 which is 2-phenyl-3-[3-(dimethylamino)propionyl]-7-methylbenzofuran.

6. A compound as defined in claim 1 which is 2-phenyl-3-[3-(dimethylamino)propionyl]-5-chlorobenzofuran.

7. A compound as defined in claim 1 which is 2-phenyl-3-[3-(dimethylamino)propionyl]-7-chlorobenzofuran.

8. A compound as defined in claim 1 which is 2-(p-tolyl)-3-[3-(dimethylamino)propionyl]benzofuran.

9. A compound as defined in claim 1 which is 2-(p-methoxyphenyl)-3-[3-(dimethylamino)propionyl]benzofuran.

10. A compound as defined in claim 1 which is 2-(p-chlorophenyl)-3-[3-(dimethylamino)propionyl]benzofuran.

* * * * *